United States Patent [19]

Mita et al.

[11] 4,338,259

[45] Jul. 6, 1982

[54] ALPHA-HALOGENO-BETA-AMINOPROPIONITRILES OR THE MINERAL ACID SALTS THEREOF, AND PROCESSES FOR PRODUCTION THEREOF

[75] Inventors: Ryuichi Mita, Kawasaki; Akihiro Yamaguchi, Kamakura; Toshio Kato, Kawasaki; Chojiro Higuchi, Kamakura; Hisamichi Murakami, Yokohama, all of Japan

[73] Assignee: Mitsui Toatsu Chemicals, Inc., Tokyo, Japan

[21] Appl. No.: 173,715

[22] Filed: Jul. 30, 1980

[30] Foreign Application Priority Data

Aug. 3, 1979 [JP] Japan .................... 54/98633
Aug. 10, 1979 [JP] Japan .................... 54/101184
Aug. 14, 1979 [JP] Japan .................... 54/102735

[51] Int. Cl.$^3$ .................... C07C 121/43; C07C 120/00
[52] U.S. Cl. .................... 260/465.5 R
[58] Field of Search .................... 260/465.5 R

[56] References Cited

U.S. PATENT DOCUMENTS

| 2,434,507 | 1/1948 | Mostek .................... 260/465.5 R |
| 2,443,292 | 6/1948 | Bauer et al. .................... 260/465.5 R |
| 2,459,420 | 1/1949 | Erickson .................... 260/465.5 R X |
| 3,038,003 | 6/1962 | Fürst et al. .................... 260/465.5 R X |

FOREIGN PATENT DOCUMENTS 39-30152 12/1964 Japan .
46-31850 9/1971 Japan .

OTHER PUBLICATIONS

Doub et al., J. Het. Chem., (1970), vol. 7, pp. 527–535.
Burzin et al., "2-Cyano-aziridin," Angew. Chem., vol. 84, p. 108 (1972).

*Primary Examiner*—Joseph Paul Brust
*Attorney, Agent, or Firm*—Fisher, Christen & Sabol

[57] ABSTRACT

A process for producing an alpha-halogeno-beta-aminopropionitrile which comprises reacting an alpha,beta-dihalogenopropionitrile with ammonia in water and/or an organic solvent. Action of a mineral acid on the reaction product gives a mineral acid salt of an alpha-halogeno-beta-aminopropionitrile. An isolated alpha-halogeno-beta-aminopropionitrile and a sulfate thereof are also provided.

15 Claims, No Drawings

ALPHA-HALOGENO-BETA-AMINOPROPIONITRILES OR THE MINERAL ACID SALTS THEREOF, AND PROCESSES FOR PRODUCTION THEREOF

This invention relates to processes for producing alpha-halogeno-beta-aminopropionitriles and the mineral acid salts thereof. More specifically, this invention relates to a process for producing an alpha-halogeno-beta-aminopropionitrile which comprises reacting an alpha,beta-dihalogenopropionitrile with ammonia in water and/or an organic solvent, and to a process for producing a mineral acid salt of an alpha-halogeno-beta-aminopropionitrile by the action of a mineral acid on the alpha-halogeno-beta-aminopropionitrile.

The present invention also relates to an alpha-halogeno-beta-aminopropionitrile and its sulfate which are novel compounds not isolated heretofore.

Alpha-halogeno-beta-aminopropionitriles and alpha-halogeno-beta-aminopropionitrile sulfates are novel compounds not isolated heretofore. These compounds are useful as intermediates for production of medicines or agricultural chemicals and for general organic syntheses. Hydrolysis of these compounds yields useful compounds convertible to alpha-halogeno-beta-alanines which are useful as intermediates for synthesis of alpha-amino acids such as serine.

In the past, alpha-halogeno-betaaminopropionitriles have been isolated in the form of the hydrochloride or benzoyl compound of alpha-chloro-beta-aminopropionitrile. For example, the method described in Japanese Patent Publication No. 30152/64 comprises reacting alpha-chloroacrylonitrile with aqueous ammonia, and treating the product with benzoyl chloride to isolate alpha-chloro-beta-benzoylpropionitrile. L. Doub et al., J. Heterocyclic Chem., Vol. 7, pp. 527–535 (June 1970) disclose isolating alpha-chloro-beta-aminopropionitrile hydrochloride in a yield of about 55% by dissolving ammonia gas in methanol, reacting alpha-chloroacrylonitrile with the solution, distilling off the unreacted ammonia and methanol under reduced pressure, adding 25% methanolic hydrochloride to the residue at a temperature of as low as $-45°$ C. to $-35°$ C., and treating the product with ether. However, both of these methods are not entirely satisfactory for commercial practice because the reaction operation is complex and the yield of the final product is low.

It has been desired therefore to develop an effective process for isolating a free alpha-halogeno-beta-aminopropionitrile and the mineral acid salt, especially the sulfate, of the alpha-halogeno-beta-aminopropionitrile.

It is an object of this invention to provide a novel process for producing an alpha-halogeno-beta-aminopropionitrile and a mineral acid salt thereof.

Another object of this invention is to provide an industrially advantageous process for producing a mineral acid salt of an alpha-halogeno-beta-aminopropionitrile.

Still another object of this invention is to provide an alpha-halogeno-beta-aminopropionitrile of the formula

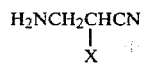

wherein X represents a halogen atom, and an alpha-halogeno-beta-aminopropionitrile sulfate of the formula

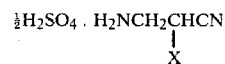

wherein X represents a halogen atom.

According to this invention, a mineral acid salt of an alpha-halogeno-beta-aminopropionitrile mineral acid salt can be produced in an almost pure form in a high yield of at least 80% by reacting an alpha,beta-dihalogenopropionitrile with ammonia in water and/or an organic solvent and treating the resulting reaction mixture containing the alpha-halogeno-beta-aminopropionitrile with a mineral acid, or extracting the alpha-halogeno-beta-aminopropionitrile from the reaction mixture using a water-immiscible organic solvent and treating it with a mineral acid.

According to this invention, an alpha-halogeno-beta-aminopropionitrile can be isolated by distilling under a reduced pressure of 1 mmHg or less the reaction mixture containing alpha-halogeno-beta-aminopropionitrile obtained by reacting an alpha,beta-dihalogenopropionitrile with ammonia in water and/or an organic solvent.

Reaction of the alpha,beta-dihalogenopropionitrile with ammonia in accordance with this invention has not been known in the past. The process of this invention is advantageous and of great industrial significance in that the yield of the desired alpha-halogeno-beta-aminopropionitrile mineral acid salt can be increased greatly and the reaction operation can be markedly simplified. Another feature of this invention is that the starting alpha,beta-dihalogenopropionitrile can be very easily prepared by halogenating alpha-acrylonitrile.

In the process of this invention, the alpha,beta-dihalogenopropionitrile is used as a starting material. It may be any of chlorine, bromine, iodine and fluorine derivatives. Alpha,beta-dichloropropionitrile and alpha,beta-dibromopropionitrile are preferred.

Ammonia is used usually in the form of aqueous ammonia. Or it may be used in the form of a solution prepared by dissolving ammonia gas or aqueous ammonia in an organic solvent.

The reaction of the alpha,beta-dihalogenopropionitrile with ammonia proceeds in water and/or an organic solvent. For convenience of isolation of the product, aqueous ammonia or an organic solvent solution of ammonia is generally used.

The organic solvent in which the reaction is carried out is an organic solvent capable of dissolving ammonia, for example a lower alcohol such as methanol, ethanol, n-propanol, isopropanol, n-butanol, isobutanol, tert-butanol, methyl Cellosolve or Cellosolve. These organic solvents may be used singly or in combination with each other. The organic solvent may also be used as a mixture with water.

The amount of ammonia used is at least 2 moles, preferably at least 2.2 moles, per mole of the alpha,beta-dihalogenopropionitrile. When the reaction is carried out in aqueous ammonia, ammonia is used in a concentration of 5 to 30% by weight. When the reaction is carried out in an organic solvent, ammonia is used in a concentration of 2 to 25% by weight.

There is no particular restriction on the method and sequence of adding the starting material and solvent in performing the reaction for forming an alpha-halogenobeta-aminopropionitrile in the process of this invention. Usually, it is preferred to employ a method which comprises gradually adding the alpha,beta-dihalogenopropionitrile to water and/or an organic solvent containing ammonia.

The reaction temperature is usually −40° to +30° C., preferably −20° to +20° C., and the reaction time is usually 0.5 to 20 hours, preferably 1 to 15 hours. The atmosphere in which the reaction is performed may be air. Use of an inert gas such as a nitrogen atmosphere or nitrogen stream is preferred because it leads to inhibition of side-reactions.

The end point of the reaction can be rapidly and easily determined by gas chromatography, high-speed liquid chromatography, etc.

The following procedures (1) to (4), for example, are used to isolate an alpha-halogeno-beta-aminopropionitrile or its mineral acid salt from the reaction mixture obtained by the reaction of the alpha,beta-dihalogenopropionitrile with ammonia in the process of this invention.

(1) When the reaction is carried out in aqueous ammonia, the alpha-halogeno-beta-aminopropionitrile is isolated from the reaction mixture as follows:

The excess of ammonia is removed from the reaction mixture by blowing nitrogen gas into it. Then, the resulting alpha-halogeno-beta-aminopropionitrile is extracted using a water-immiscible organic solvent, and dried over anhydrous sodium sulfate, anhydrous magnesium sulfate, etc. The alpha-halogeno-beta-aminopropionitrile is distilled under a vacuum of 1 mmHg or less. Common organic solvents may be used as the water-immiscible organic solvent. Examples include aromatic hydrocarbons such as benzene, toluene and xylene; halogenated hydrocarbons such as dichloromethane, chloroform, carbon tetrachloride, dichloroethane, trichloroethane, tetrachloroethane, trichloroethylene, tetrachloroethylene, chlorobenzene and o-dichlorobenzene; alcohols such as n-butanol and isobutanol; ketones such as methyl isobutyl ketone and diisobutyl ketone; and esters such as methyl acetate, ethyl acetate and butyl acetate.

(2) When the above reaction is carried out in an organic solvent. The resulting alpha-halogeno-beta-aminopropionitrile is isolated from the reaction mixture as follows:

The reaction mixture is filtered to remove the by-product ammonium halide, and the residue is treated in the same way as in procedure (1).

(3) When the reaction is carried out in aqueous ammonia, the mineral acid salt of alpha-halogeno-beta-aminopropionitrile is isolated from the reaction mixture as follows:

The alpha-halogeno-beta-aminopropionitrile is extracted from the reaction mixture, for example, by using a water-immiscible organic solvent. A mineral acid is caused to act on the extract to precipitate the mineral acid salt of alpha-halogeno-beta-aminopropionitrile. Alternatively, the excess of ammonia is removed from the reaction mixture by a suitable method, for example by blowing nitrogen gas into it. Then, the reaction mixture is mixed with a large excess of a water-miscible organic solvent containing a mineral acid to precipitate the mineral acid salt of the alpha-halogeno-beta-aminopropionitrile. Examples of the water-immiscible organic solvent used to extract the alpha-halogeno-beta-aminopropionitrile include aromatic hydrocarbons such as benzene, toluene and xylene; halogenated hydrocarbons such as dichloromethane, chloroform, carbon tetrachloride, dichloroethane, trichloroethane, tetrachloroethane, trichloroethylene, tetrachloroethylene, chlorobenzene and o-dichlorobenzene; alcohols such as n-butanol and isobutanol; ketones such as ethyl isobutyl ketone and diisobutyl ketone; and esters such as methyl acetate, ethyl acetate and butyl acetate.

(4) When the above reaction is carried out in an organic solvent, the mineral acid salt of the alpha-halogeno-beta-aminopropionitrile is isolated from the reaction mixture as follows:

The excess of ammonia is removed from the reaction mixture by a suitable method, for example by blowing nitrogen gas into it. Then, the by-product ammonium halide is removed by filtration, and the reaction mixture is treated with a mineral acid to precipitate the mineral acid salt of the alpha-halogeno-beta-aminopropionitrile.

The mineral acid used in the procedures (3) and (4) to convert the alpha-halogeno-beta-aminopropionitrile into its mineral acid salt may be hydrochloric acid, sulfuric acid, nitric acid, phosphoric acid, etc. Hydrochloric acid and sulfuric acid are preferred. Hydrochloric acid may be in the form of an aqueous solution of hydrogen chloride. Preferably, it is used in the form of a solution prepared by dissolving hydrogen chloride in a water-miscible organic solvent such as methanol, ethanol, n-propanol, isopropanol, n-butanol, isobutanol, methyl Cellosolve, Cellosolve, tetrahydrofuran or dioxane. Sulfuric acid is used in a concentration of 80 to 100%. Preferably, it is used in the form of a solution prepared by dissolving sulfuric acid in a water-miscible organic solvent such as methanol, ethanol, n-propanol, isopropanol, n-butanol, isobutanol, methyl Cellosolve, Cellosolve, tetrahydrofuran or dioxane. The amount of the mineral acid may be slightly in excess of the theoretical amount. It is not necessary to use it in a large excess.

The organic solvent for dissolving the mineral acid is used in an amount usually 0.5 to 10 times, preferably 1 to 5 times, the amount of the mineral acid.

A specific operation for treating the alpha-halogeno-beta-aminopropionitrile with the mineral acid to precipitate its mineral acid salt may be the gradual dropwise addition of an organic solvent solution of the mineral acid to the reaction mixture containing the alpha-halogeno-beta-aminopropionitrile or to the aforesaid extract, or the gradual addition of the extract or reaction mixture containing the alpha-halogeno-beta-aminopropionitrile to an organic solvent solution of the mineral acid. Preferably, the treatment is effected while maintaining the temperature of the liquid at not more than 50° C., especially not more than 30° C. In this manner, the mineral acid salt of alpha-halogeno-beta-aminopropionitrile having a very high purity can be isolated in a yield of as high as at least 80%.

The following Examples illustrate the present invention more specifically. All percentages in these examples are by weight.

EXAMPLE 1

Ammonia gas was dissolved in isopropanol so that the concentration of ammonia became 6.4%. Five hundred grams of the isopropanol solution of ammonia was cooled to 0° C., and in an atmosphere of nitrogen, 62 g of alpha,beta-dichloropropionitrile was added dropwise with stirring over the course of about 2 hours. The reaction was carried out for 3 hours at 0° to 5° C. Nitrogen gas was blown into the reaction mixture at the same temperature to remove the excess of ammonia. Then, the by-product ammonium chloride was removed by filtration. To the filtrate was gradually added dropwise 88 g of an isopropanol solution of hydrogen chloride in a concentration of 25%. The crystals that precipitated were separated by filtration, washed with isopropanol, and dried to afford 60.8 g (yield 86.2% based on the alpha,beta-dichloropropionitrile) of alpha-chloro-beta-aminopropionitrile hydrochloride.

Melting point: 154°–155° C. (decomp.).

| Elemental analysis values (%) for $C_3H_5N_2Cl \cdot HCl$: | | | | |
| --- | --- | --- | --- | --- |
| | C | H | N | Cl |
| Found: | 25.34 | 4.35 | 19.98 | 50.42 |
| Calculated: | 25.55 | 4.29 | 19.87 | 50.29 |

EXAMPLE 2

The procedure of Example 1 was repeated except that 58 g of an isopropanol solution of conc. sulfuric acid having a sulfuric acid concentration of 50% was used instead of the isopropanol solution of hydrogen chloride in Example 1. Specifically, a solution prepared by dissolving 29 g of 98% sulfuric acid in 29 g of isopropanol was gradually added dropwise at less than 10° C. to the reaction mixture. The precipitated white crystals were separated by filtration, washed with isopropanol, and dried to afford 65.3 g (yield 85% based on the alpha-chloroacrylonitrile) of alpha-chloro-beta-aminopropionitrile sulfate having a melting point of 181° to 182° C. (decomp.). Recrystallization of the product from a mixture of water and isopropanol gave pure alpha-chloro-beta-aminopropionitrile sulfate having a melting point of 182° to 183° C. (decomp.).

| Elemental analysis values (%) for $C_3H_5N_2Cl \cdot \frac{1}{2}H_2SO_4$: | | | | | |
| --- | --- | --- | --- | --- | --- |
| | C | H | N | Cl | S |
| Found: | 23.38 | 3.92 | 18.38 | 23.21 | 10.21 |
| Calculated: | 23.46 | 3.94 | 18.24 | 23.08 | 10.44 |

Infrared absorption spectrum $(cm^{-1})$: 2250, 1580, 1485, 1441, 1398, 1240, 1110, 1038, 900.

Proton NMR spectrum ($D_2O$, measuring temperature: room temperature):
δ Values (ppm)
3.76 (2H, doublet)
5.36 (1H, triplet)

EXAMPLE 3

243 g of conc. aqueous ammonia (ammonia concentration 28%) was cooled to 0° C., and with vigorous stirring in an atmosphere of nitrogen, 124 g of alpha,-beta-dichloropropionitrile was added dropwise over the course of about 2 hours, and they were reacted at this temperature for 4 hours. Nitrogen gas was blown into the reaction mixture to remove the excess of ammonia. The reaction mixture was then filtered to remove the by-product ammonium chloride. The filtrate was extracted three times with 300 ml of 1,2-dichloroethane to separate alpha-chloro-beta-aminopropionitrile. All of the extracts were combined, dried over anhydrous sodium sulfate, and filtered. While the filtrate was cooled at less than 10° C., a solution of 62 g of 100% sulfuric acid in 125 g of isopropanol was gradually added dropwise to it. The precipitated crystals were separated by filtration, washed with isopropanol, and dried to afford 122.9 g (yield 80% based on alpha-chloro-acrylonitrile) of alpha-chloro-beta-aminopropionitrile sulfate having a melting point of 180° to 181° C. (decomp.).

The product showed the same infrared absorption spectrum as that obtained in Example 1.

EXAMPLE 4

The reaction mixture left after removing the excess of ammonia in Example 3 was added to 2000 g of an isopropanol solution containing 60 g of conc. sulfuric acid at less than 20° C. The precipitate was separated by filtration to give 126 g (yield 82% based on alpha-chloroacrylonitrile) of alpha-chloro-beta-aminopropionitrile sulfate having a melting point of 180° to 181° C. (decomp.).

EXAMPLE 5

122 g of conc. aqueous ammonia (ammonia concentration 28%) was cooled to 0° C., and with vigorous stirring in an atmosphere of nitrogen, 62 g of alpha,beta-dichloropropionitrile was added dropwise over the course of 2 hours. They were reacted at this temperature for 4 hours. Nitrogen gas was blown into the reaction mixture to remove the excess of ammonia. Then, the reaction mixture was extracted three times with 200 ml of 1,2-dichloroethane. The extracts were combined and dried over anhydrous sodium sulfate. Sodium sulfate was filtered, and while the filtrate was stirred at less than 10° C., 90 g of an isopropanol solution of hydrogen chloride having a hydrogen chloride concentration of 25% was gradually added dropwise to it. The precipitated crystals were separated by filtration, washed with isopropanol, and dried to afford 57.8 g (yield 82% based on alpha,beta-dichloropropionitrile) of alpha-chloro-beta-aminopropionitrile hydrochloride having a melting point of 153° to 154.5° C. (decomp.).

EXAMPLE 6

The procedure of Example 5 was repeated except that 60 g of isopropanol solution of conc. sulfuric acid having a sulfuric acid concentration of 50% was used instead of the isopropanol solution of hydrogen chloride. Thus, 62.2 g (yield 81% based on alpha,beta-dichloropropionitride) of alpha-chloro-beta-aminopropionitrile sulfate having a melting point of 179° to 181° C. (decomp.) was obtained.

EXAMPLE 7

243 g of conc. aqueous ammonia (ammonia concentration 28%) was cooled to 0° C., and with vigorous stirring in an atmosphere of nitrogen, 124 g of alpha,-beta-dichloropropionitrile was added dropwise over the course of about 2 hours. They were further reacted at 0° to 5° C. for 4 hours. Nitrogen gas was blown into the reaction mixture to remove the excess of ammonia. The resulting alpha-chloro-beta-aminopropionitrile was separated from the reaction mixture by extracting it three times with 300 ml of 1,2-dichloroethane. The extracts were combined, and dried over anhydrous sodium sulfate, and filtered. The filtrate was distilled at reduced pressure to afford 62 g of alpha-chloro-beta-aminopropionitrile.

Boiling point: 53°–54° C./0.8 mmHg.

| Elemental analysis values (%) for $C_3H_5N_2Cl$: | | | | |
| --- | --- | --- | --- | --- |
| | C | H | N | Cl |
| Found: | 34.35 | 4.96 | 26.78 | 33.86 |

-continued

| Elemental analysis values (%) for $C_3H_5N_2Cl$: | | | |
|---|---|---|---|
| C | H | N | Cl |
| Calculated: 34.47 | 4.82 | 26.80 | 33.91 |

Infrared absorption spectrum: 3395 cm$^{-1}$ and 3305 cm$^{-1}$ ($\nu NH_2$), 2240 cm$^{-1}$ ($\nu C\equiv N$).

Proton NMR spectrum (acetone-Db, measuring temperature: room temperature)
δ Values (ppm):
3.71 (2H, doublet),
5.98 (1H, triplet)

Mass spectrum (measuring temperature 60° C.): m/e: 103, 76, 69, 42, 30.

EXAMPLE 8

500 g of an isopropanol solution of ammonia prepared by dissolving ammonia gas in isopropanol to an ammonia concentration of 6.4% was cooled to 0° C. With stirring in an atmosphere of nitrogen, 62 g of alpha,beta-dichloropropionitrile was added dropwise over the course of 2 hours. They were further reacted at 0° to 5° C. for 3 hours. Nitrogen was blown into the reaction mixture at the same temperature to remove the excess of ammonia. Then, the by-product ammonium chloride was removed by filtration. The filtrate was distilled under reduced pressure to afford 29 g of alpha-chloro-beta-aminopropionitrile as a fraction having a boiling point of 52° to 53° C./0.75 mmHg.

What we claim is:

1. A process for producing a mineral acid salt of alpha-halogeno-beta-aminopropionitrile comprising reacting alpha,beta-dihalogenopropionitrile with at least two moles of ammonia per mole of alpha,beta-dihalogenopropionitrile in water, in an organic solvent, or in a mixture of water and an organic solvent at a temperature of −40° C. to +30° C., and then reacting the reaction product with a mineral acid selected from the group consisting of hydrochloric acid, sulfuric acid, nitric acid, and phosphoric acid to convert said reaction product to said salt.

2. The process of claim 1 wherein said alpha,beta-dihalogenopropionitrile is alpha,beta-dichloropropionitrile.

3. The process of claim 1 wherein said organic solvent is an ammonia-soluble organic solvent.

4. The process of claim 1 wherein said mineral acid is hydrochloric acid.

5. The process of claim 1 wherein said mineral acid is sulfuric acid.

6. A process for producing a mineral acid salt of alpha-halogeno-beta-aminopropionitrile comprising reacting alpha,beta-dihalogenopropionitrile with at least two moles of ammonia per mole of alpha,beta-dihalogenopropionitrile in water at a temperature of −40° C. to +30° C., separating the resulting alpha-halogeno-beta-aminopropionitrile from the reaction mixture by extraction with a water-immiscible organic solvent, and then treating the extract with a mineral acid selected from the group consisting of hydrochloric acid, sulfuric acid, nitric acid, and phosphoric acid to convert said alpha-halogeno-beta-aminopropionitrile to said salt.

7. A process for producing a mineral acid salt of alpha-halogeno-beta-aminopropionitrile comprising reacting alpha,beta-dihalogenopropionitrile with at least two moles of ammonia per mole of alpha,beta-dihalogenopropionitrile in an organic solvent or in a mixture of it with water at a temperature of −40° C. to +30° C., separating the by-product ammonium halide by filtration, and treating the filtrate with a mineral acid selected from the group consisting of hydrochloric acid, sulfuric acid, nitric acid, and phosphoric acid to form said salt.

8. A process for producing a mineral acid salt of alpha-halogeno-beta-aminopropionitrile comprising reacting alpha,beta-dihalogenopropionitrile with at least two moles of ammonia per mole of alpha,beta-dihalogenopropionitrile in water at a temperature of −40° C. to +30° C., and treating the reaction mixture with a water-miscible organic solvent containing a mineral acid selected from the group consisting of hydrochloric acid, sulfuric acid, nitric acid, and phosphoric acid to form said salt.

9. A process for producing alpha-halogeno-beta-aminopropionitrile comprising reacting alpha,beta-dihalogenopropionitrile with at least two moles of ammonia per mole of alpha,beta-dihalogenopropionitrile in water, in an organic solvent, or in a mixture of water and an organic solvent at a temperature of −40° C. to +30° C., extracting the reaction mixture with a water-immiscible organic solvent to separate the alpha-halogeno-beta-aminopropionitrile, and distilling the extract at a vacuum of 1 mmHg or less.

10. The process of claim 1 wherein said alpha,beta-dihalogenopropionitrile is alpha,beta-dibromopropionitrile.

11. The process of claim 1 wherein said temperature is −20° C. to +20° C.

12. A process as claimed in claim 1, 6, 7, or 8 wherein said mineral acid is selected from the group consisting of hydrochloric acid and sulfuric acid.

13. A process as claimed in claim 1, 7, 8, or 9 wherein said reaction with ammonia is in a mixture of organic solvents.

14. A process as claimed in claim 1, 7, or 9 wherein the ammonia is used in water in a concentration of 5 to 30% by weight and is used in an organic solvent in a concentration of 2 to 25% by weight.

15. A process as claimed in claim 6 or 8 wherein the ammonia is used in water in a concentration of 5 to 30% by weight.

* * * * *